United States Patent [19]

Kirsch

[11] Plant 5,201

[45] Mar. 6, 1984

[54] LILY NAMED PINK SENSATION

[75] Inventor: Ted T. Kirsch, Myrtle Point, Oreg.

[73] Assignee: Sun Valley Bulb Farms, Inc., Myrtle Point, Oreg.

[21] Appl. No.: 422,201

[22] Filed: Sep. 23, 1982

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Chas. W. Rummler

[57] ABSTRACT

A new and distinct variety of lily plant of the Parkmanni type Oriental Hybrid, particularly distinguished by its large, generally pink outwardly facing flowers with white edged, recurved petals each having a dark, more red mid-rib extending from the base almost to the tip. The flowers on this plant are borne in a raceme arrangement on tall, strong stems and long, outwardly projecting pedicels, usually with one bud or flower on each pedicel. This plant also has dark green and relatively disease-resistant foliage as observed where lily diseases do occur.

2 Drawing Figures

BACKGROUND OF THE NEW PLANT

This new variety of lily plant originated as a seedling of unknown parentage growing in nursery at Arcata, Calif. Its large, pink outwardly facing flowers and dark green, apparently disease-resistant, foliage prompted me to propagate this new plant for study. I have found advantageous and distinctive characteristics in this new plant which make it a valuable addition to the field of commercial lily cut flower culture. Propagation of this new lily through successive generations by means of scales and tissue culter at Arcata, Calif. has shown that its distinctive characteristics hold true from generation to generation and appear to be firmly fixed.

DESCRIPTION OF THE DRAWING

My new variety of lily plant is illustrated by the accompanying photographic drawing, which in full color shows a full grown blossoming stem in the lower view and a closeup of several blooms in the upper view which show more of the flower detail and its formation. The color rendition in these views is as nearly true as can reasonably be obtained by conventional photographic procedures.

DESCRIPTION OF THE NEW PLANT

The following is a detailed description of my new variety of lily plant with color designations according to the R.H.S. Colour Chart published by The Royal Horticultural Society of London, England. The observations for this description were made on greenhouse grown plants at Arcata, Calif. in the spring of 1982.

THE PLANT

Origin: Seedling.
Parentage: Unknown.
Classification:
- *Botanic.*—Oriental Hybrid — Parkmanni type.
- *Commercial.*—Lily for cut flowers.

Form: A tall, single stem growing vertically upward from each, single-nose bulb.
Height: About 3 to 4½ feet at maturity.
Growth: Sturdy and upright with excellent strength.

Cane diameter: From about ¼ inch growing from a small bulb to about ½ inch for a stem arising from a large bulb.
Foliage:
- *Number of leaves.*—Two, one at the base of each pedicel and one on the pedicel 2 to 3 inches from the flower.
- *Size.*—About 4½ to 6 inches long and from 1½ to 2 inches wide.
- *Shape.*—Lanceolate.
- *Texture.*—Leathery.
- *Aspect.*—Smooth.
- *Ribs and veins.*—The leaves have distinct parallel veins extending from base to tip.

Bulblets (On underground stem):
- *Occurrence.*—1 to 3 on each healthy, normal plant at digging time.
- *Size.*—From ¼ inch to 1 inch in diameter.
- *Color.*—White, with occasional pink shading at the tips.

Bulbs:
- *Size.*—From ½ inch to 12 inches in circumference, depending on the age.
- *Color.*—White, with yellow and pink overtones. As the bulbs become larger and older, the overtones of yellow and pink become more and more prominent.

THE BUD

Form: Elliptic with acute apex.
Size:
- *Length.*—About 4 to 4½ inches.
- *Diameter.*—About 1¼ to 1½ inches.

Number: Usually one on each pedicel; There may be as many as 12 buds on a single plant according to its culture and the bulb size.
Opening rate: Normal; Buds open successively from the lowermost bud to the top bud which is the last to open.
Color: When the sepals first divide and petals begin to unfurl: Red Purple 70-C; Generally, the mid-rib is redder on the sepals and greenish red on the petals.
Surface texture: Rugose and leathery, with prominent veins.
Pedicels:

*Character.*—Strong and generally projecting outwardly at an angle of about 45° from the vertical with the buds slightly inclined downardly.

*Color.*—Light Green on the bottom side and Green with Maroon splotches on the top side.

*Aspect.*—Glabrous and glaucous.

*Length.*—About 5 to 7 inches.

THE FLOWER

Blooming habit: Annually; Blooming profusely in July when grown outdoors.

Size of flower: Large — averaging about 8 inches in diameter.

Borne:

*From large bulbs.*—The inflorescence has a raceme arrangement with each pedicel bearing one bud, and with 3 to 6 blooms open at one time. The size of the bulb and its cultural care will determine the number of blooms and buds to be found in any normal inflorescence.

Shape: Almost flat with petals spaced uniformly in a star arrangement and with about the outer quarter of the petal length being recurved.

Petalage: Normal — 3 sepals and 3 petals.

*Form.*—Ovate with obtuse apex and a center furrow bisecting each petal longitudinally, the petal edges being slightly undulate.

*Size.*—Petals are about 5 inches long and about 2¼ inches wide.

*Texture.*—Leathery.

*Aspect.*—Velvety.

*Color.*—Upper side: Upon opening, the petal is R.H.S. Red Purple 66-D. The mid-rib is darker and more red like R.H.S. 63-A. The outer ⅛ edge of the entire petal is white R.H.S. 155-C, and the basal half of the petal on each side of the mid-rib is covered with numerous dark maroon spots. The nectary is Yellow Green R.H.S. 144-B. The sepals are more narrow and have fewer spots than the petals. Under Side: Petals R.H.S. 65-C with ⅛ inch white edging. Sepals R.H.S. 70-C with the mid-rib being redder.

*Papillae.*—Present on petals and 5 to 10 in number.

Fragrance: Sweet.

Discoloration: The color darkens somewhat as the blossom matures.

Effect of weather: The flowers are generally not affected by wet weather, but the flower ages faster as the temperature rises.

Persistence: The flower tends to hang on and dry.

Lasting quality:

*On the plant.*—2 or 3 weeks depending on the size of the bulb and its environmental temperature.

*As a cut flower.*—10 to 14 days.

REPRODUCTIVE ORGANS

Stamens: 6 in number and arranged orderly around the pistil.

*Anthers.*—Length — about ⅞ inches. Color — Yellow Orange R.H.S. 23-A.

*Filaments.*—Length — about 3 inches. Color — Light Green.

Pistil:

*Number.*—One.

*Style.*—Length — about 2½ inches. Color — Light Green at the base; Darker Green at the top.

*Stigma.*—Color — Light Green.

Ovary character: Classified as a schizocarp, about 1½ inches long and about 1 inch in diameter, dehiscing into thirds and containing 6 rows of seeds of the usual shape for lilies.

I claim:

1. A new and distinct variety of Oriental Hybrid lily, substantially as herein shown and described, characterized by its large generally pink outwardly facing flowers having white edged recurved petals moderately covered with dark maroon spots, the flowers being borne on long, strong outwardly and upwardly projecting pedicels and long lasting whether on the plant or as cut flowers and the foliage is dark green.

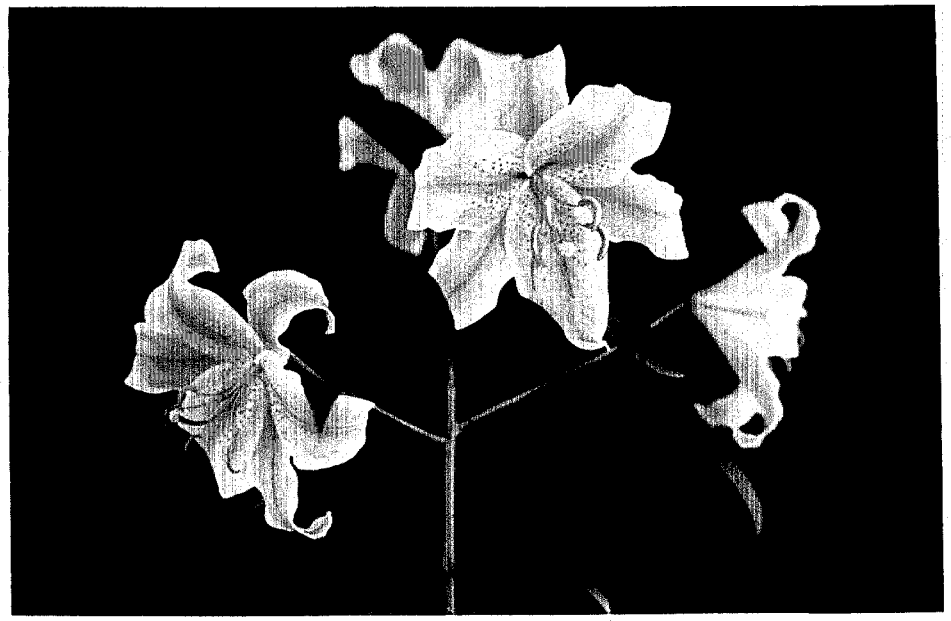
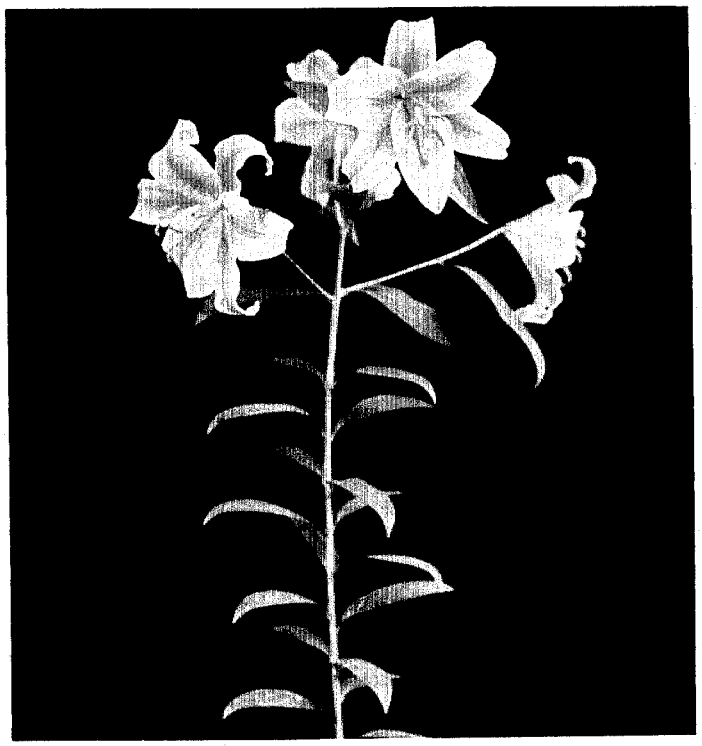

* * * * *